United States Patent

Yamaguchi et al.

[11] Patent Number: 5,820,877
[45] Date of Patent: Oct. 13, 1998

[54] PERCUTANEOUSLY ADMINISTRABLE PATCH PREPARATION

[75] Inventors: Hisashi Yamaguchi; Hiroyuki Maeda; Yoshirou Kamihoriuchi, all of Tsukuba, Japan

[73] Assignee: Hisamitsu Pharmaceutical Co., Inc., Tosu, Japan

[21] Appl. No.: 663,186

[22] PCT Filed: Mar. 10, 1995

[86] PCT No.: PCT/AU95/00124

§ 371 Date: Jun. 14, 1996

§ 102(e) Date: Jun. 14, 1996

[87] PCT Pub. No.: WO95/16440

PCT Pub. Date: Jun. 22, 1995

[51] Int. Cl.$^6$ .............................. A61L 15/16; A61K 9/70
[52] U.S. Cl. ........................... 424/449; 424/446; 424/448
[58] Field of Search ............................ 424/449; 604/896, 604/897, 448; 514/415, 416, 923

[56] References Cited

U.S. PATENT DOCUMENTS

| | | | |
|---|---|---|---|
| 4,245,630 | 1/1981 | Lloyd et al. | 128/155 |
| 4,687,481 | 8/1987 | Nuwayser | 604/897 |

FOREIGN PATENT DOCUMENTS 0 208 395 A1  1/1987  European Pat. Off. .

Primary Examiner—Thurman K. Page
Assistant Examiner—Kathryne E. Shelborne
Attorney, Agent, or Firm—Kubovcik & Kubovcik

[57] ABSTRACT

A percutaneous or permucosal patch drug preparation. The preparation includes: (1) a backing layer impermeable to a drug component, (2) a drug storage layer which holds the drug component therein and is situated under the central portion of the backing layer, (3) a protective film which is impermeable to the drug component, has notches and is situated under the drug storage layer and the peripheral portion of the backing layer, (4) a pressure-sensitive adhesive layer which is situated under the protective film, and (5) a releasable liner layer which is impermeable to the drug component and situated under the pressure-sensitive layer. When the releasable liner layer is peeled off of the preparation, the protective film is torn along the notches and the portion of the protective film surrounded by the notches is removed together with the releasable liner layer and a portion of the adhesive between the protective film and the releasable liner layer. The patch drug preparation is held on the skin or mucosa of a patient by the pressure-sensitive adhesive remaining on the peripheral portion of the protective film. The drug held in the drug storage layer is released directly to the mucosa or to the skin.

6 Claims, 5 Drawing Sheets

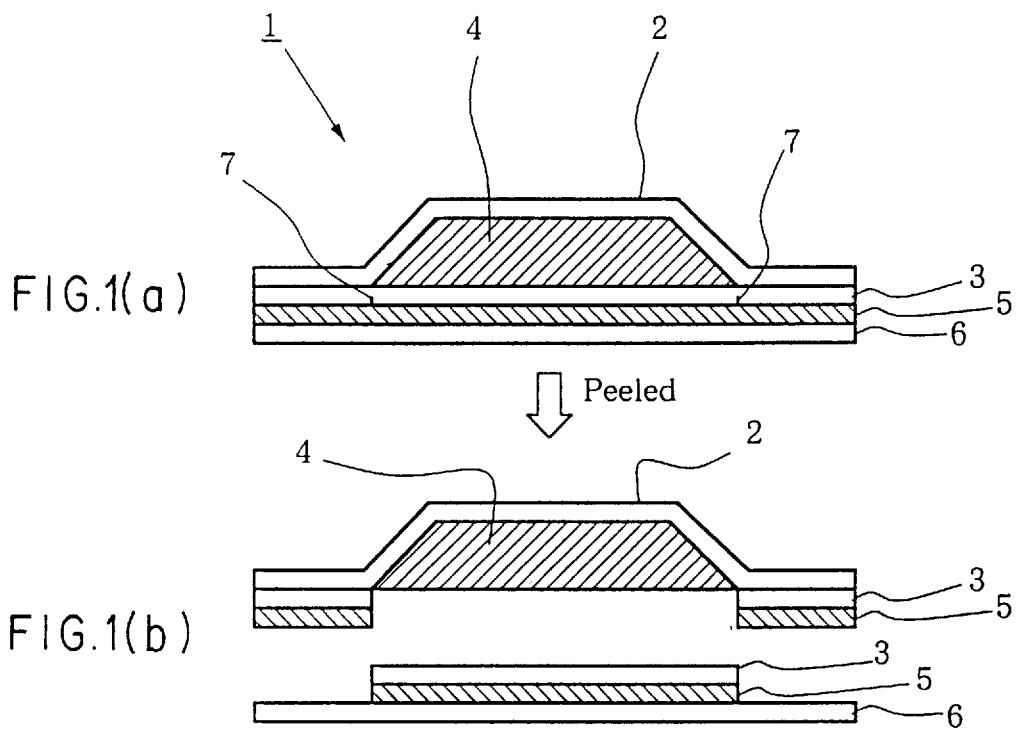
FIG.1(a)
Peeled
FIG.1(b)
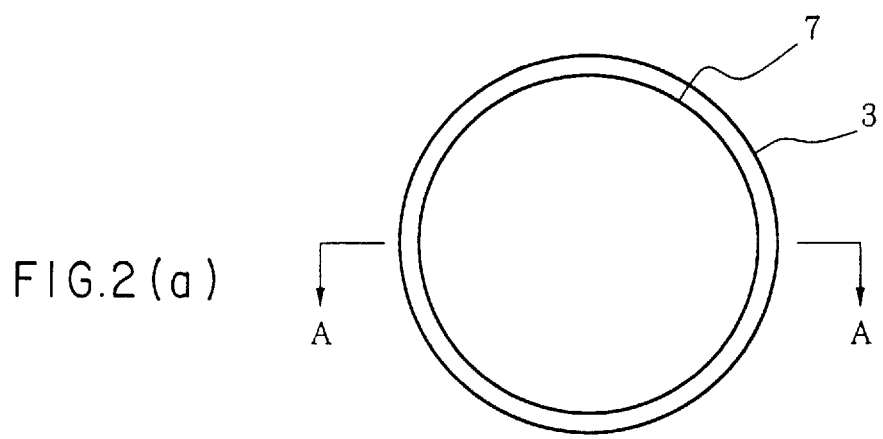
FIG.2(a)
FIG.2(b)

PERCUTANEOUSLY ADMINISTRABLE PATCH PREPARATION

This application is a 35 USC 371 of PCT/JP93/01808 filed Dec. 14, 1993.

TECHNICAL FIELD

This invention relates to a field of medicinal remedy using a percutaneously administrable drug preparation. More particularly it relates to a percutaneously administrable patch drug preparation (the preparation being hereinafter referred to as a "percutaneous patch drug preparation" for brevity) which can maintain the stability of a drug contained in the preparation during storage thereof by effectively inhibiting the drug from leaking and evaporation from the preparation.

BACKGROUND ART

Preparations which are percutaneously or permucosally administered have recently been thought much of as a means for administering a drug to patients. Such preparations as above are able to be administered to the systemic and all local portions of the skin of the patients and enable a controlled fixed amount of the drug to be continuously administered for a long period of time.

Preparations which enable their drug to be percutaneously administered, are generally classified into matrix-type ones in which a drug is dispersed in an adhesive layer, and reservoir-type ones which have a drug storage layer. A typical matrix-type percutaneous drug preparation which is well known at present, includes such a one as described in Japanese Patent Gazette No. Sho 57-59806 (or 59806/82), while a typical reservoir-type percutaneous drug preparation known well at present includes such a one as disclosed in Japanese Patent Gazette No. Sho 54-16566 (or 16566/79). The reservoir-type drug preparation has a drug storage layer in which are enclosed a fixed amount of a drug, at least one kind of a solvent, an absorption accelerator, a solubilizer, a stabilizer, a viscosity-enhancing agent and the like, each preliminarily designed or predetermined, for the purpose of administering the drug so that a controlled dose of the drug is continuously circulated in the body for a fixed period of time.

The structure of a conventional reservoir-type drug preparation, however, is such that the drug is likely to leak or evaporate through an inhibitive film of the preparation during storage of the preparation before administration thereof whereby the amount of the drug is lessened as compared with the predetermined one at the time of administering the preparation to a patient. This will result in that the purpose of the percutaneous drug preparation for administering a predetermined amount of the drug systemically and continuously is not attained. In order to solve problems the conventional percutaneous patch drug preparation has had, there are developed, for example, a preparation having a drug reservoir provided at its upper and lower portions respectively with films which protect from solvent, a preparation which has a drug storage layer closely enclosed in a film protecting the drug from various environmental factors and allows the drug storage layer to be exposed by peeling a releasable liner when the preparation is used, and a preparation wherein its drug storage layer is sealed in an aluminum-made laminate film during preservation of the preparation, and the laminate film is removed prior to the use of the preparation thereby to increase the stability of the drug during the storage thereof. The above preparations so developed are each complicated in structure and any of them still do not solve the problems.

In addition, a percutaneous patch drug preparation described in Japanese Pat. Appln. Laid-Open Gazette No. Hei 2-1283 (No. 1283/90) is illustrated in FIG. 9 of the accompanying drawings. This preparation so illustrated is characterized in that the drug is prevented from leaking and evaporation from the preparation during the preservation thereof by providing a second releasable heat-sealed portion 11 around the periphery surrounding an area through which the drug will permeate when the preparation is used. When the preparation is used by a patient, a releasable liner layer 6 together with an inner liner layer 9 is removed since the adhesion strength between the releasable heat seal 11 and the inner liner layer is weaker than that between the releasable liner layer 6 and the inner liner layer 9, thereby to form a patch for releasing the drug therethrough. In this percutaneous patch drug preparation, the drug cannot entirely be sealed in the reservoir layer whereby it is not made entirely possible to prevent the drug from leakage and evaporation during the preservation of the preparation. In said FIG. 9, numeral 1 represents a percutaneous patch drug preparation, numeral 2 a backing layer, numeral 4 a drug storage layer, numeral 5 a pressure-sensitive adhesive, numeral 8 a film layer and numeral 10 a first releasable heat seal. Like numerals represent like parts, respectively, in the other Figures.

In such a conventional percutaneous patch drug preparation wherein the pressure-sensitive adhesive is situated under the inhibitive film, an interaction is caused between the drug and the adhesive since the drug passes through the adhesive layer on the way from the inhibitive film to the skin for percutaneous absorption, whereupon it is likely to exert serious effects on the continuous and uniform administration of the drug and cause the degradation of the pressure-sensitive adhesive.

DISCLOSURE OF THE INVENTION

An object of this invention is to solve the problems the conventional percutaneous patch drug preparations have heretofore raised and to provide novel percutaneous or permucosal patch drug preparations which enable a predetermined does of a drug to be stably and continuously administered percutaneously to the systemic and all portions of the skin.

Another object of this invention is to provide a percutaneous patch drug preparation which can stably preserve therein an initial designed amount of a drug without a loss thereof until the preparation is administered to a patient.

Still another object of this invention is to provide a percutaneous patch drug preparation which enables the drug to be percutaneously administered without being affected by a pressure-sensitive adhesive contained in the preparation.

MEANS FOR SOLVING THE PROBLEMS

These objects are attained by the provision of a percutaneous patch drug preparation having a protective film which is able to be torn into a predetermined shape with aid of notches provided on said film.

More particularly, this invention resides in a percutaneous or permucosal patch drug preparation which comprises:

(1) a backing layer impermeable to a drug component, (2) a drug storage layer containing the drug component, which is situated under the central portion of the backing layer, (3) a protective film impermeable to the drug component, which has notches and is situated under the drug storage layer and the peripheral portion of the backing layer, (4) a pressure-sensitive adhesive layer which is situated under the protective film and (5) a releasable liner layer which is situated under the pressure-sensitive adhesive layer and is impermeable to the drug component.

This invention will be explained in more detail with reference to the accompanying drawings.

FIG. 1 in the drawings is a sectional view showing an example of a percutaneous patch drug preparation of this invention. FIG. 1(a) shows the state of the preparation prior to its use, and FIG. 1(b) the state thereof subsequent to removal of the releasable liner layer for use of the preparation. In FIG. 1, the protective film and the notches are designated at 3 and 7, respectively.

In FIG. 1, the backing layer 2 is situated in the uppermost part of the percutaneous patch drug preparation 1. The backing layer has a hollow for holding and preserving the drug therein as required. The outside shape of the backing layer and the shape of the hollow are not particularly limited and, however, they may generally be circular or elliptic in shape.

The material of the backing layer must be impermeable to all of the drugs enclosed in the drug storage layer. In other words, the material is required to be impermeable to the drug components enclosed therein, and examples of the material are plastic films made of polyethylene, polypropylene, polyethylene terephthalate, polyvinyl chloride, polyvinylidene chloride, plasticized vinyl acetate copolymers (such as plasticized vinyl acetate vinyl chloride copolymer), polyamide (nylon) and so on; and cellulose films made of cellophane, cellulose acetate, ethylcellulose and so on. These films may each be laminated with an aluminum foil or may have thereon an aluminum layer formed by vacuum deposition or a ceramic coat. Although the backing layer is not particularly limited in shape, it must be a shape capable of holding at least the drug storage layer therein, the shape being such as a cup-like one.

As illustrated in FIG. 1, the drug storage layer 4 containing a drug component is provided under the central portion of the backing layer 2.

The component to be contained in the drug storage layer 4 may be a drug component alone or a multi-component drug comprising one or more members of solvents, absorbefacients, solubilizers, stabilizers, viscosity-enhancing agents and so on in addition to a drug component. The drug is enclosed in the drug storage layer in the form of a solution, dispersion, gel or solid. These components may be enclosed therein respectively in necessary amounts as required.

The drug component to be used may be any percutaneously absorbable drug which exhibits a curative or prophylactic effect when applied to the skin of a patient, and several examples of such a drug will now be listed.

(a) coronary vasodilators such as nitroglycerin and isosorbide dinitrate, (b) antihypertensive agents such as clonidine hydrochloride and nifedipine, (c) narcotic analgesics such as morphine hydrochloride and fentanyl citrate, (d) anti-inflammatory agents such as ketoprofen, indomethacin, ketorolac, loxoprofen, tenidap and buprenorphine hydrochloride, (e) bronchodilators such as isoproterenol sulfate, salbutamol sulfate and tulobuterol hydrochloride, (f) androgenic hormones such as testosterone propionate and fluoxymesterone, (g) follicle hormones such as estradiol benzoate, ethinylestradiol and estriol, (h) corpus luteum hormones such as progesterone, norethisterone and levonorgestrel, (i) antiallergic agents such as sodium cromo-glicate, azelastine and ketotifen fumarate, (j) muscle relaxants such as eperisone hydrochloride and afloqualone, (k) antihistamic agents such as diphenhydramine and d,1-chlorpheniramine maleate, (l) general anesthetics such as thiopental sodium and ketamine hydrochloride, (m) antitussive expectorants such as codeine phosphate and ephedrine hydrochloride, (n) antivertigo agents such as difenidol hydrochloride and betahistine mesylate, and (o) assistants for quitting smoking such as nicotine.

If necessary, two or more of the foregoing percutaneously absorbable drugs may be used jointly. Further, these drugs may also be enclosed in the drug storage layer in the form of esters, amides or acetals derived therefrom or medically acceptable inorganic or organic salts thereof.

Such a derivative or salt is converted into its active form when subjected in vivo to the action of an enzyme, pH change or the like. The amount a particular drug to be contained in the drug storage layer is, per se, so determined as to give a predetermined drug concentration in blood continuously over a necessary period of time. The sizes of the patch and the medically effective surface area thereof are determined depending on the amount of the drug thus determined.

In the drug storage layer, a solvent composed of ethanol or ethanol/water is generally used as the base in an amount of 0 to 40% by weight. Further, such a drug as described above is added to the base generally in an amount of up to 40% by weight. Further, various additives may be added to the base, and they include viscosity-enhancing agents such as cellulose acetate, methylcellulose, hydroxypropylcellulose, hydroxypropylmethylcellulose, polyvinyl alcohol, polyvinylpyrrolidone, acrylic acid, sodium carboxymethylcellulose and stearyl alcohol; solubilizers and solubilizer assistants such as crotamiton, ethylene glycol, diethylene glycol, triethylene glycol, propylene glycol, polyethylene glycol, polypropylene glycol, dimethyl sulfoxide, dimethylformamide, dimethylacetamide, dimethyl-laurylamide, isosorbitol, olive oil, castor oil, squalene and lanolin; emulsifying agents such as phosphatidic acid derivatives, lecithin, cephalin and polyalkylene glycols; absorbefacients such as methyl laurate, methyl caprylate, azone, oleic acid, 1-menthol, limonene and mentha oil; and torpents such as glycerol monooleate, glycerol monolaurate and sorbitan monolaurate. With respect to these additives, the most suitable kind and concentration for use with a particular drug are determined within such a range as recognized to be therapeutically effective and pharmacologically acceptable.

As illustrated in FIG. 1, the protective film 3 which is impermeable to the drug component and has notches is provided under the drug storage layer 4 and the peripheral portion of the backing layer 2. The protective film serves to inhibit the drug from leaking and evaporating from the above drug storage layer 4 during the preservation of the preparation until the application thereof to a patient.

The protective film 3 must be impermeable to all of the components contained in the drug storage layer and is preferably one which is heat-sealable to the backing layer 2. The material of such an impermeable protective film includes plastic films made of polyethylene, polypropylene, polyethylene terephthalate, polyvinyl chloride, polyvinylidene chloride, plasticized vinyl acetate copolymers (such as plasticized vinyl acetate-vinyl chloride copolymer) and polyamide; and cellulose films made of cellophane, cellulose acetate and ethylcellulose. Further, the material may also be any of these films which is improved in barrier properties by laminating it with an aluminum foil, by forming an aluminum layer thereon by vacuum deposition or by coating the film with a ceramic. Among these films, it is preferably to use a film difficult to tear in any planar direction.

As illustrated in FIG. 1, the protective film 3 must have notches 7 which cause the film itself to be torn into a predetermined shape when necessary. The notches 7 of the protective film may be provided either on the side facing the drug storage layer 4 and the peripheral portion of the backing layer 2 or on the side facing the pressure-sensitive adhesive layer 5.

The plan and sectional views of an example of the protective film 3 are shown respectively in FIGS. 2(a) and (b). In this example, as illustrated in these figures, the notches 7 are provided by cutting the protective film 3 halfway in the thickness direction by the use of a die cutting blade, and the notches must not pierce the protective film through at any portion. The protective film 3 may be either a single-layer one or a laminated one composed of two or more layers. For example, the protective film may be a laminated film as illustrated in FIG. 2 which is composed of the films 31 and 32 and is notched from the side of the film 31. In this case, the film 32 is generally made of a material heat-sealable to both the film layer which will be described below an the backing film.

FIGS. 3(a) and (b) show the plan and sectional views of a second example of the protective film to be used in this invention, respectively. In this example, as illustrated in these figures, perforations 71 are employed as the notches. Such perforations 71 can easily be made by die cutting or the like.

FIGS. 4(a) and (b) show the plan and sectional views of a third example of the protective film to be used in this invention respectively. As illustrated in these figures, a lengthwise slit 72 for making the tearing of the protective film start more smoothly may be provided in addition to the above employment of perforations 71 as the notches 7.

The protective film 3 serves to inhibit the drug from leaking and evaporating from the drug storage layer 4 of the percutaneous patch drug preparation during the preservation of the preparation until the preparation is applied to a patient, while it is torn into a predetermined shape just before the application thereof to a patient to form a path for releasing the drug. The protective film 3 and the peripheral portion of the backing layer 2 are preferably bonded to each other by heat sealing which can generally make a bonded product resistant to delamination for a long period of time, though a method of the bonding is not limited.

As illustrated in FIG. 1, the pressure-sensitive adhesive layer 5 is provided over the whole undersurface of the protective film 3. The adhesive to be used may be any one which can make the percutaneous patch drug preparation hold on the skin or mucosa of a patient only by the peripheral portion of the upper half of FIG. 1(b) of the preparation, has an adhesive strength high enough to hold, as one body (the lower half of FIG. 1(b)), a portion of the protective film separated therefrom by being torn along the notches and the releasable liner layer 6 with the adhesive remaining between said film portion and the liner layer, and is acceptable both dermatologically and mucosologically. Several examples of such an adhesive will now be described.

The examples are acrylic type adhesives such as poly-2-ethylhexyl acrylate; methacrylic type adhesives such as polybutyl methacrylate; silicone type adhesives such as polydimethylsiloxane; rubber type adhesives such as polyisoprene rubber, polyisobutylene rubber, polybutadiene rubber and natural rubber; cellulose derivatives; and natural rubber.

As illustrated in FIG. 1, the releasable liner layer 6 is situated under the pressure-sensitive adhesive layer 5. The releasable liner layer covers the whole undersurface of the percutaneous patch drug preparation and may have a tab for peeling, if necessary. The material constituting the releasable liner layer must be impermeable to the drug, and examples of the material are plastic films and cellulose films as described above with respect to the material constituting the backing layer.

According to this invention, as illustrated in FIG. 1(b), when the releasable liner layer 6 is attempted to be peeled off, the protective layer is torn along the notches whereby the portion of the protective film 3 surrounded by the notches is removed with the peripheral portion of the film 3 being left on the percutaneous patch drug preparation. Accordingly, in applying the preparation to a patient, the pressure-sensitive adhesive layer 5 situated under the protective film 3 is left only in the peripheral portion, i.e., it is absent in the path for releasing the drug toward the skin. This permits the release of the drug without the drug and the pressure-sensitive adhesive exerting any adverse effect on each other.

FIG. 5 is a sectional view of a second example of the percutaneous patch drug preparation 1 of this invention, wherein numeral 8 refers to a film layer.

The percutaneous patch drug preparation 1 illustrated in FIG. 5 is different from that illustrated in FIG. 1 in that the film layer 8 is present between the peripheral portion of the backing layer 2 or the drug storage layer 4, and the protective film 3 in addition to the constituents shown in FIG. 1. The porosity and pore size of the film may be suitably selected for each drug depending on the object of control. It is generally preferably to bond the backing layer 2, the film layer 8 and the protective film 3 to each other by heat sealing which can make a bonded product resistant to delamination for a long period of time, though a method of the bonding is not limited.

The material constituting the film layer 8 may be generally a drug-permeable resin which can be bonded to the above backing layer 2, and the following materials can be used.

The material includes plastic films made of polyolefins (such as polyethylene and polypropylene), polyester, polycarbonate, polyvinyl chloride, polyamide, polyimide, polyacrylonitrile, polystyrene derivatives, ethylene-vinyl acetate copolymer, ethylene-polyvinyl alcohol copolymer, fluororesins, acrylic resins and epoxy resins; cellulose films made of cellulose and so on; and porous rubber sheets made of foamed polyisoprene rubber and so on.

FIG. 6 is a sectional view showing a third example of the percutaneous patch drug preparation 1 of this invention, wherein number 6a refers to a non-release treated portion and numeral 6b a portion treated therewith.

The percutaneous patch drug preparation 1 illustrated in FIG. 6 is such as the one illustrated in FIG. 1, but is different from the latter in that the portion (6b) of the surface of the releasable liner layer 6 being in contact with the pressure-sensitive adhesive layer 5 is treated with a release agent.

Precisely, the portion (6a) of the surface of the releasable liner layer 6 which is in contact with the pressure-sensitive adhesive layer 5 corresponding to the portion of the protective film 3 to be torn and removed is non-release treated, while the portion (6b) of the surface thereof which is in contact with the pressure-sensitive layer 6 and is to be peeled from the pressure-sensitive adhesive layer 5 is release treated. By employing this constitution, the adhesive strength between the pressure-sensitive adhesive layer 5 and the releasable liner layer 6 in the portion corresponding to the portion of the protective film 3 which is torn along the notches 7 into a predetermined shape and removed is increased, while that between the layers 5 and 6 is decreased in the peripheral portion 6b. This makes it possible to tear the protective film 3 more smoothly along the notches 7 into a predetermined shape. The release agents to be used for the release treatment include silicones and fluorocarbons.

FIG. 7 is a sectional view showing a fourth example of the percutaneous patch drug preparation 1 of this invention, wherein numeral 61 refers to a first releasable liner layer and numeral 62 a second releasable liner layer.

In the patch preparation illustrated in FIG. 7, the releasable liner layer is composed of two layers, and the first releasable liner layer (film) 61 which is impermeable to the drug, has been punched to remove its portion equivalent to or somewhat smaller than a portion of the protective film 3 to be torn and removed and is then laminated on the adhesive-side surface 6b with a release-treated film, is provided on the second releasable liner layer (film) 62. This constitution makes it easier to tear the protective film along the notches into a predetermined shape.

Although the percutaneous patch drug preparation of this invention is not particularly limited in shape, it is at least necessary that the drug contained in the drug storage layer is effectively released toward the skin or mucosa of the human body. Further, the effective area of the percutaneous patch drug preparation through which the percutaneous or permucosal administration of the drug component is carried out, in other words, the opening of the undersurface of the drug storage layer varies depending upon the necessary amount of the drug to be released. The effective area suitable for attaining a therapeutic does is 2 to 30 cm$^2$, preferably 3 to 10 cm$^2$. On the other hand, the whole area of the surface of the percutaneous patch drug preparation to be brought into contact with the skin or mucosa of the human body, in other words, the area of the adhesive layer before peeling the releasable liner layer with the removal of a part of the protective layer and the like must be generally about 1.5 to 2.0 times the above effective area in order to attain good adhesion. Accordingly, the above whole area is preferably 5 to 60 cm$^2$, more preferably 7.5 to 30 cm$^2$.

In the percutaneous patch drug preparation of this invention, the protective film is torn into a predetermined shape, so that when the preparation is applied to a patient, the pressure-sensitive adhesive layer is present only in the peripheral portion of the preparation, i.e., it is absent in the path for releasing the drug toward the skin. By virtue of this characteristic, the drug and the adhesive do not exert any adverse effect on each other and thus permit the advantageous release of the drug for percutaneous administration. Further, during the preservation of the preparation until the administration thereof to a patient, the migration of the drug component contained in the drug storage layer to the pressure-sensitive adhesive layer is so inhibited as to cause neither lowering in the amount of the drug nor deterioration of the pressure-sensitive adhesive.

The percutaneous patch drug preparation of this invention is freed from leakage or evaporation of the drug from the drug storage layer during the preservation of the preparation by employing a protective film having notches. During the preservation of the preparation, this protective film can completely closely enclose the drug in the drug storage layer owing to the unpeelable heat seal made around the periphery surrounding the effective area which the drug will permeate. In applying the preparation to a patient, the protective film is torn along the notches owing to the adhesion between the protective film and the releasable liner to form a path for releasing the drug.

BRIEF DESCRIPTION OF DRAWINGS

FIG. 1 is a sectional view showing an example of the percutaneous patch drug preparation of this invention, wherein FIG. 1(a) shows the state of the preparation prior to its use, while FIG. 1(b) the state thereof subsequent to removable of the releasable liner layer for use of the preparation;

FIGS. 2(a) and 2(b) are planar and sectional views showing an example of the protective film to be used in this invention.

BEST MODE FOR CARRYING OUT THE INVENTION

The following examples further illustrate this invention, though this invention is not limited to them.

EXAMPLE 1

Figure 7:
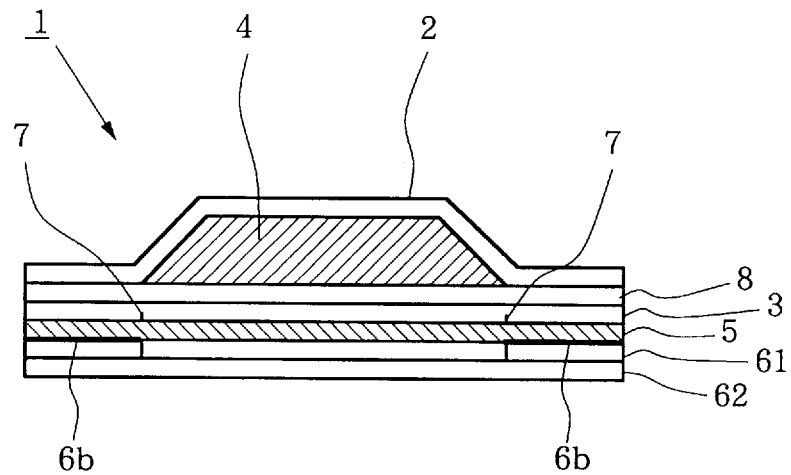
FIG. 7 is a sectional view showing a fourth example of the percutaneous patch drug preparation of this invention.

A percutaneous patch drug preparation 1 as illustrated in FIG. 7 was prepared as follows.

Three parts by weight of a hardening agent (a product of Soken Chemical Engineering Co., Ltd., trade name: L-45) were added to 100 parts by weight of a commercially available acrylic pressure-sensitive adhesive (a product of Soken Chemical Engineering Co., Ltd., trade name: SK Dyne 1259) and the obtained mixture was sufficiently agitated to give an acrylic pressure-sensitive adhesive.

This pressure-sensitive adhesive was applied on a 36 μm thick polyethylene terephthalate film by coating in a thickness of 4 mil and heated to 90° C. for 10 minutes. The exposed surface of the resulting 36 μm thick polyethylene terephthalate film was coated with a silicone release agent and an elliptic piece of 5 cm² in area was die-cut out of the film thereby to form a first releasable liner layer 61. The thus formed first releasable liner layer 61 was laminated with a second releasable liner layer (polyethylene terephthalate film) 62 to form a releasable liner layer 6. The acrylic pressure-sensitive adhesive prepared above was applied on the releasable liner layer 6 by coating in a thickness of 4 mil and heated to 90° C. for 10 minutes to form a pressure-sensitive adhesive layer 5.

Separately, an elliptic piece of 5 cm² was die-cut out of a 50 μm thick composite resin film made of polyethylene and polyethylene terephthalate. Both the elliptic piece and the rest of the film were heat-sealed together to a 20 μm thick polyethylene film to form a protective film 3. Further, a porous polyethylene film (pore diameter: 0.25 μm, porosity: 78%) was used as the film 8.

A gel as prepared below was injected into the drug storage layer 4. Namely, 5.0 g of glycerol were added to 8.6 g of a phosphate buffer having a pH of 6.8, followed by sufficient stirring. Then, 0.7 g of sodium carboxymethylcellulose, 6.1 g of ethanol, 0.1 g of preliminarily molten lauryl alcohol, 0.6 g of glycerol monooleate and 0.2 g of sorbitan monolaurate were added to the mixture prepared above, followed by sufficient stirring thereby to obtain a further mixture. Further, 0.6 g of tulobuterol hydrochloride was added to the resulting further mixture and sufficiently stirred to give a gel. 0.5 ml of this gel was syringed into the drug layer. Further, a 50 μm thick composite film composed of polyethylene and polyethylene terephthalate was formed into a cup-like shape to be used as a backing layer 2.

The die-cut portion of the releasable liner layer 6 was fitted with the notch of the protective film 3, after which the backing layer 2, the film 8 and the protective film 3 were simultaneously heat-sealed around the peripheral portion of the drug storage layer 4. The obtained laminate was die-cut into an ellipse (56 mm×45 mm). Thus, the above percutaneous patch drug preparation was obtained.

EXAMPLE 2

A percutaneous patch drug preparation comprising a protective film 3 having notches 7 as illustrated in FIG. 2 was prepared as follows.

Three parts by weight of a hardening agent (a product of Soken Chemical Engineering Co., Ltd., trade name: L-45) were added to 100 parts by weight of a commercially available acrylic pressure-sensitive adhesive (a product of Soken Chemical Engineering Co., Ltd., trade name: SK Dyne 1259) and the obtained mixture was sufficiently agitated to give an acrylic pressure-sensitive adhesive.

The thus given acrylic pressure-sensitive adhesive was applied by coating in a thickness of 4 mil on a 125 μm thick releasable liner layer (polyethylene terephthalate film) 6 which had been treated with a silicone release agent with only a circular portion of 5 cm² being left untreated, and the whole was heated to 90° C. for 10 minutes to form a pressure-sensitive adhesive layer 5.

A cellophane/aluminum foil/polyethylene composite film having a thickness of 70 μm was notched by a die cutter fitted with a 0.8 mm thick blade having the edge dulled into the form of a circle of 5 cm². Thus, a protective film 3 having notches 7 was obtained. Further, a 50 μm thick porous polyethylene film (pore diameter: 0.25 μm, porosity: 78%) was used as the film 8.

A gel prepared below was injected into the drug layer 4, Namely, 0.4 g of fentanyl citrate was added to 8.5 g of a phosphate buffer having a pH of 6.8, followed by the addition of 4.8 g of ethanol, 5 g of glycerol, 0.1 g of lauryl alcohol, 0.5 g of glycerol monooleate, 0.2 g of sorbitan monolaurate and 0.8 g of sodium carboxymethylcellulose. The mixture thus obtained was sufficiently stirred and 0.5 ml of the resulting mixture was syringed into the drug layer.

Furthermore, a 50 μm thick composite film composed of polyethylene and polyethylene terephthalate was formed into a cup-like shape to be used as the backing layer 2. The non-treated circular portion of 5 cm² of the releasable liner layer 6 was fitted with the notch of the protective film, and thereafter, the backing layer 2, the film 8 and the protective film 3 were simultaneously heat-sealed around the peripheral portion of the drug layer 4 and the resulting laminate was die-cut into a circle having a diameter of 45 mm. Thus, the above percutaneous patch drug preparation was obtained.

EXAMPLE 3

Figure 3A:
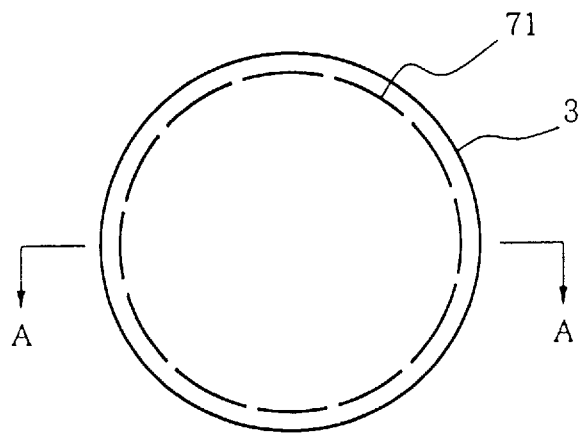
FIGS. 3(a) and 3(b) are planar and sectional views showing a second example of the protective film to be used in this invention.
Figure 3B:
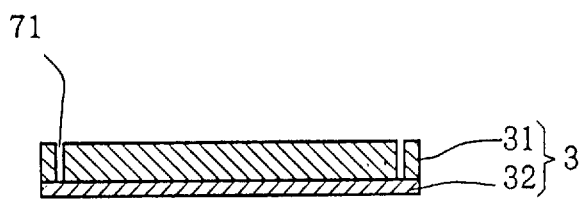

A percutaneous patch drug preparation comprising a protective film having notches (perforations 71) as illustrated in FIG. 3 was prepared as follows. Perforations 71 were made on a 70 μm thick composite film 31 composed of nylon and linear low-density polyethylene by the use of a die cutter fitted with a circular blade having a thickness of 0.7 mm, a diameter of 25.23 mm and 0.3 mm wide slits every 11.25 degrees. The resulting perforated composite film 31 was heat bonded to a 20 μm thick polyethylene film 32 under the conditions of 130° C., 3 seconds and 6 kg/cm², with the polyethylene side being faced to the film 32.

A gel prepared as below was injected into the drug layer 4. Namely, 0.2 g of buprenorphine hydrochloride was added to 8.7 g of a phosphate buffer having a pH of 4.0, followed by sufficient stirring. Then, 4.8 g of ethanol, 5 g of polyethylene glycol, 0.1 g of lauryl alcohol, 0.6 g of glycerol monooleate, 0.2 g of sorbitan monolaurate and 0.6 g of hydroxypropylmethylcellulose were added to the mixture prepared above. The obtained mixture was sufficiently stirred and 0.5 ml of the resulting mixture was syringed into the drug layer.

The subsequent steps were conducted in the same manner as that of Example 2. Thus, the above percutaneous patch drug preparation was obtained.

EXAMPLE 4

A percutaneous patch drug preparation comprising a protective film 3 having notches (perforations 71) as illustrated in FIG. 3 was prepared as follows.

A laminated film composed of a 12 μm thick polyethylene terephthalate film and a 30 μm thick linear low-density polyethylene film was perforated by the use of a circular die cutting blade having 0.1 mm wide slits every 5 degrees and a diameter of 25.23 mm to form a film 31 having perforations 71. This film 31 was dry-laminated with a 15 μm thick polyethylene film 32 to form a protective film 3.

The subsequent steps were conducted in the same manner as those of Example 3. Thus, the above percutaneous patch drug preparation was obtained.

EXAMPLE 5

A percutaneous patch drug preparation comprising a protective film 3 having notches (perforations 71) as illustrated in FIG. 3 was prepared as follows.

Perforations 71 were made on a 50 μm thick cross-laminated film made of high-density polyethylene by the use of a circular die cutting blade having 0.1 mm wide slits every 5 degrees and a diameter of 25.23 mm to form a perforated film 31. This film 31 was dry-laminated with a 15 μm thick polyethylene film 32 to form a protective film 3.

The subsequent steps were conducted in the same manner as those of Example 3. Thus, the above percutaneous patch drug preparation was obtained.

EXAMPLE 6

Figure 4A:
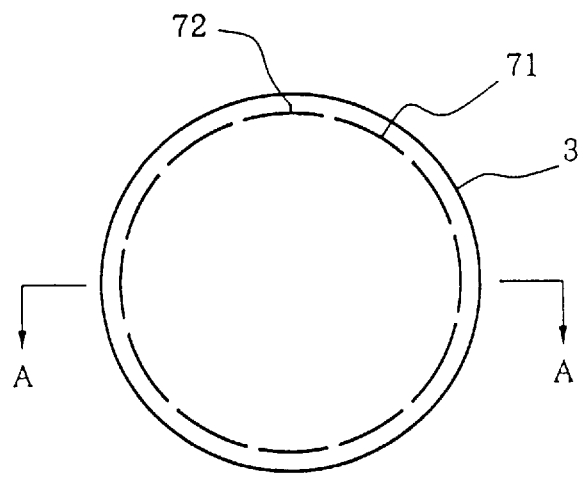
FIGS. 4(a) and 4(b) are planar and sectional views showing a third example of the protective film to be used in this invention.
Figure 4B:
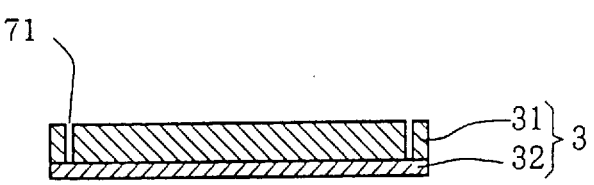
Figure 5:
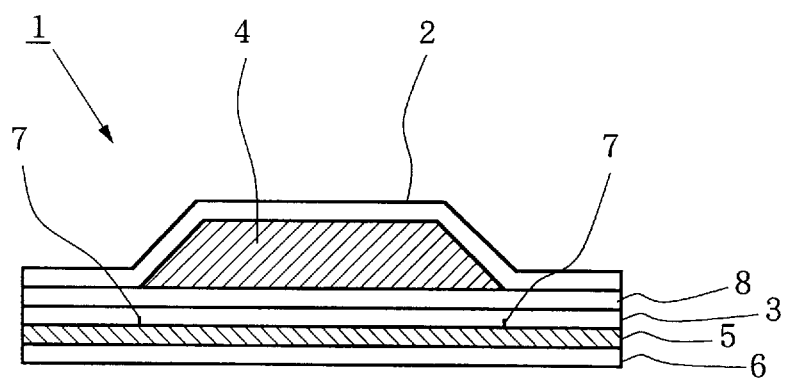
FIG. 5 is a sectional view showing a second example of the percutaneous patch drug preparation of this invention.
Figure 6:
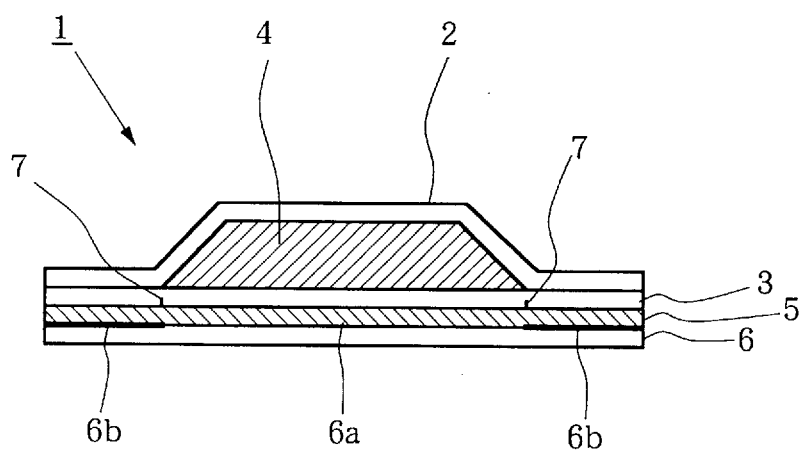
FIG. 6 is a sectional view showing a third example of the percutaneous patch drug preparation of this invention.

A percutaneously absorbable preparation comprising a protective film 3 as illustrated in FIG. 4 having a lengthwise slit 72 and perforations 71 was prepared as follows.

A lengthwise slit 72 and perforations 71 were made on a 70 μm thick composite film composed of nylon and linear low-density polyethylene by the use of a die cutter fitted with a blade having 0.3 mm wide slits every 10 degrees, 1 mm wide slits every 5 degrees from each of the 0.3 mm wide slits, and a thickness of 0.7 mm. The resulting composite film 31 was heat bonded to a 20 μm thick polyethylene film 32 under the conditions of 130° C., 3 seconds and 6 kg/cm$^2$.

A gel prepared below was injected into the drug layer 4. Namely, 24 mg of levonorgestrel was added to 9.4 g of a phosphate buffer having a pH of 6.8, followed by sufficient stirring. Then, 4.8 g of ethanol, 5 g of polyethylene glycol, 0.2 g of myristyl alcohol and 0.6 g of hydroxypropylmethylcellulose were added to the mixture prepared above and 0.5 ml of the resulting further mixture was syringed into the drug layer.

The subsequent steps were conducted in the same manner as those of Example 2. Thus, the above percutaneous patch drug preparation was obtained.

Comparative Example 1

Figure 8:
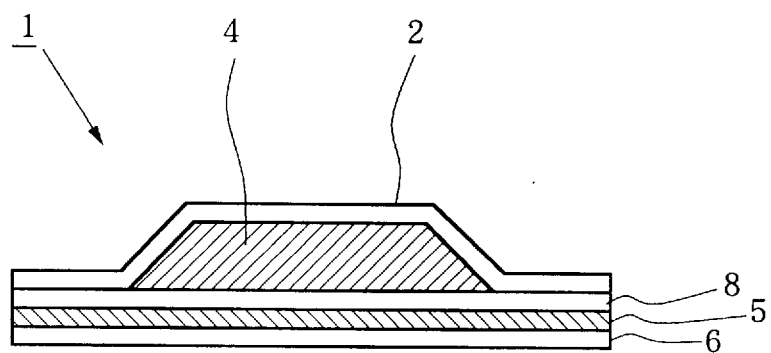
FIG. 8 is a sectional view showing an example of the percutaneous patch drug preparation of the prior art.

A percutaneous patch drug preparation as illustrated in FIG. 8 was prepared as follows.

A 36 μm thick polyethylene terephthalate film whose surface had been treated with a silicon release agent was used as the releasable liner layer 6. The same acrylic pressure-sensitive adhesive as that used in Example 1 was applied on the film by coating in a thickness of 4 mil and heated to 90° C. for 10 minutes to form a pressure-sensitive adhesive layer 5. Further, the same 50 μm-thick porous polyethylene film (pore diameter: 0.25 μm, porosity: 78%) as that used in Example 1 was used as the film 8.

0.5 ml of the same gel as that prepared in Example 1 was syringed into the drug layer.

Further, a 50 μm thick composite film composed of polyethylene film and polyethylene terephthalate film was formed into a cup-like shape to be used as the backing film 2.

The backing layer 2 and the film 8 were heat sealed to each other and the resulting laminate was die-cut into an ellipse (56 mm×45 mm). Thus, the above percutaneous patch drug preparation was obtained.

Comparative Example 2

Figure 9:
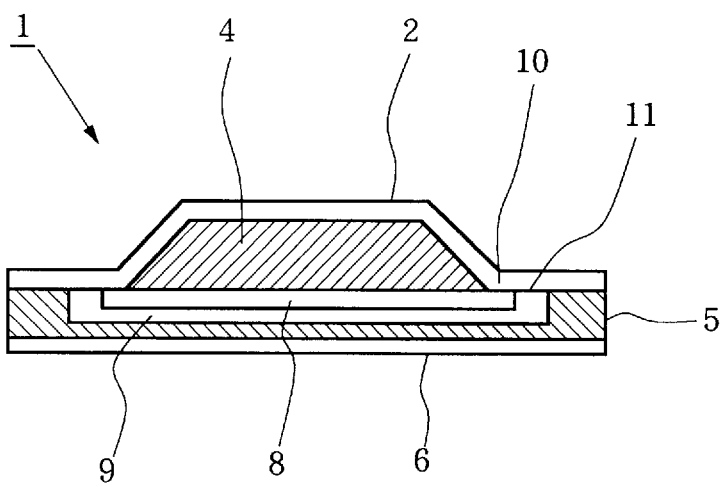
FIG. 9 is a sectional vie showing another example of the percutaneous patch drug preparation of the prior art.

A percutaneous patch drug preparation as illustrated in FIG. 9 was prepared as follows.

85 parts by weight of a commercially available acrylic pressure-sensitive adhesive (a product of Monsanto Chemical Co., trade name: GELVA 788) were mixed with 15 parts by weight of another commercially available acrylic pressure-sensitive adhesive (a product of Monsanto Chemical Co., trade name: GELVA 737) and the obtained mixture was sufficiently agitated to give an acrylic pressure-sensitive adhesive.

A 5 mil thick polyester film whose surface had been treated with a silicone release agent was used as the releasable liner layer 6. The pressure-sensitive adhesive prepared above was applied on the treated surface of the film in a thickness of 3 mil and heated to 90° C. for 10 minutes to form a pressure-sensitive adhesive layer 5.

A 4 mil thick composite film composed of polyester and ethylene-vinyl acetate copolymer was die-cut into an ellipse piece (38 mm×27 mm) to be used as the inner liner layer 9 with the polyester side being faced to the pressure-sensitive adhesive.

The same 50 μm thick porous polyethylene film (pore diameter: 0.25 μm, porosity: 78%) as that used in Example 1 was used as the film 8, and 0.5 ml of the same gel as that prepared in Example 1 was syringed into the drug layer.

Further, the same 50 μm thick composite film composed of polyethylene and polyethylene terephthalate as that used in Example 1 was formed into a cup-like shape to be used as the backing layer 2.

The backing layer 2, the film 8 and the inner liner layer 9 were heat-sealed to each other around the peripheral portion of the drug layer and the resulting laminate was die-cut into ellipse (56 mm×45 mm). Thus, the above percutaneous patch drug preparation was obtained.

Test Example 1

Drug retention test

Figure 10:
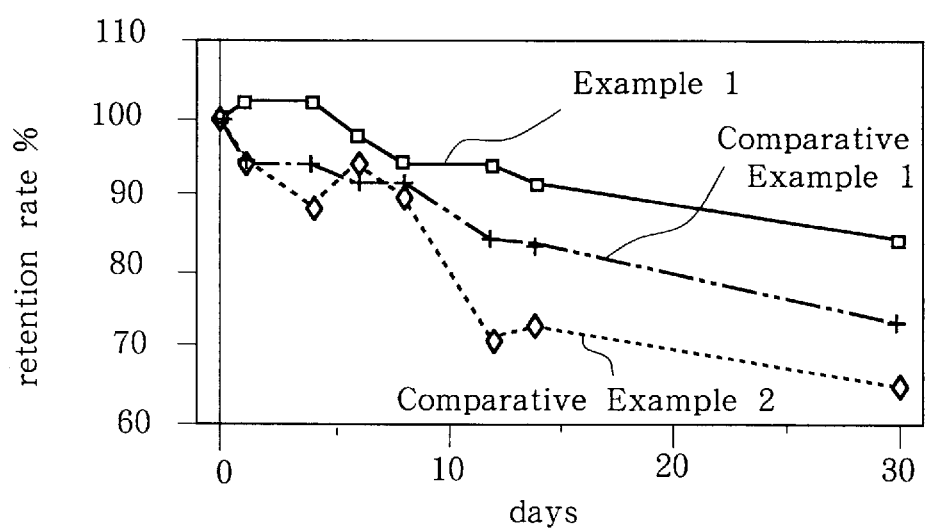
FIG. 10 is a graph showing a change with time in the retention of drug in the drug storage layer observed in a drug retention test.

The drug preparations prepared in Example 1 and Comparative Examples 1 and 2 were each put in an outer bag made of an aluminum/polyethylene composite film. The resulting bag was heat sealed and stored at 60° C. to determined the retention of the drug in the drug storage layer. The results are given in FIG. 10. It can be understood from the results given in FIG. 10 that the percutaneous patch drug preparation of Example 1 of this invention is satisfactorily inhibited from leakage and evaporation of the drug as compared with conventional ones of Comparative Examples 1 and 2.

[Industrial Applicability]

As described above, the percutaneous patch drug preparation of this invention is satisfactorily inhibited from leakage and evaporation of the drug and therefore makes it possible to percutaneously administer the drug in an initially designed dose stably, continuously and systemically. Further, the preparation can stably preserve therein the initially designed amount of a drug without a loss thereof until the preparation is administered to a patient. Furthermore, the preparation enables the drug to be percutaneously administered without any adverse effect brought about by a pressure-sensitive adhesive contained in the preparation.

The percutaneous patch drug preparation of this invention having these excellent features exhibits aimed curative effects sufficiently as a percutaneous patch drug preparation containing a percutaneously absorbable drug when applied to the skin or mucosa of a human body, thus being extremely useful in medical industry.

What is claimed is:

1. A percutaneous or permucosal patch drug preparation which comprises, in combination:
    (1) a backing layer impermeable to a drug component and having a hollow portion and a peripheral portion,
    (2) a drug storage layer which holds a drug component therein and is provided in said hollow portion of the backing layer, (3) a protective film which is impermeable to the drug component and is situated under said drug storage layer and adhered to the peripheral portion of the backing layer, said protective film having notches provided partway in the thickness direction of the film, said notches surrounding a portion of said film situated below said drug storage layer, (4) a pressure-sensitive adhesive layer which is adhered to the protective film, and (5) a releasable liner layer which is impermeable to the drug component and is provided on the pressure-sensitive adhesive layer.

2. A percutaneous or permucosal patch drug preparation which comprises, in combination:

(1) a backing layer impermeable to a drug component and having a hollow portion and a peripheral portion;

(2) a drug storage layer which holds a drug component therein and is provided in said hollow portion of the backing layer;

(3) an intermediate film situated under said drug storage layer and adhered to the peripheral portion of the backing layer;

(4) a protective film adjacent to said intermediate film, said protective film being impermeable to the drug component and having notches provided partway in the thickness direction of the film, said notches surrounding a portion of said film situated below said drug storage layer, (5) a pressure-sensitive adhesive layer which is adhered to the protective film, and (6) a releasable liner layer which is impermeable to the drug component and is provided on the pressure-sensitive adhesive layer.

3. A percutaneously administrable patch drug preparation according to claim 1 or 2, wherein the drug component is percutaneously absorbable to a patient.

4. A percutaneously administrable patch drug preparation according to claim 1 or 2, wherein the releasable liner is wholly releasable without leaving releasable only a portion of said liner layer which corresponds to a portion of the protective film which is between the notches provided therein.

5. A percutaneously administrable patch drug preparation according to claim 1 or 2, wherein the protective film is a laminated film prepared by laminating a film having a perforation of a predetermined shape with a sealable film.

6. A percutaneously administrable patch drug preparation according to claim 1 or 2, wherein the notches of the protective film are situated below the peripheral portion of the drug storage layer and have a shape of an annular groove to thereby enable the film to be torn into a predetermined shape for release of the drug when administered.

* * * * *

UNITED STATES PATENT AND TRADEMARK OFFICE
CERTIFICATE OF CORRECTION

PATENT NO.   : 5,820,877
DATED        : Oct. 13, 1998
INVENTOR(S)  : Hisashi YAMAGUCI et al.

It is certified that error appears in the above-indentified patent and that said Letters Patent is hereby corrected as shown below:

On the Title page, left column, item [22] (PCT filed), delete "Mar. 10, 1995" and insert therefor --Dec. 14, 1993--, and item [86] (PCT No.), delete "PCT/AU95/00124" and insert therefor --PCT/JP93/01808--.

Signed and Sealed this

Twenty-fourth Day of August, 1999

*Attest:*

Q. TODD DICKINSON

*Attesting Officer*        Acting Commissioner of Patents and Trademarks